United States Patent
Reicher

(10) Patent No.: US 10,747,403 B2
(45) Date of Patent: Aug. 18, 2020

(54) ADAPTABLE USER INPUT INTERFACE

(71) Applicant: International Business Machines Corporation, Armonk, NY (US)

(72) Inventor: Murray A. Reicher, Rancho Santa Fe, CA (US)

(73) Assignee: International Business Machines Corporation, Armonk, NY (US)

( * ) Notice: Subject to any disclaimer, the term of this patent is extended or adjusted under 35 U.S.C. 154(b) by 249 days.

(21) Appl. No.: 15/670,107

(22) Filed: Aug. 7, 2017

(65) Prior Publication Data

US 2019/0042062 A1 Feb. 7, 2019

(51) Int. Cl.

| | | |
|---|---|---|
| *G06F 3/0482* | (2013.01) | |
| *G06F 19/00* | (2018.01) | |
| *G16H 30/20* | (2018.01) | |
| *G16H 40/63* | (2018.01) | |
| *G06F 3/0481* | (2013.01) | |
| *G06F 9/451* | (2018.01) | |
| *G06F 3/0488* | (2013.01) | |

(52) U.S. Cl.
CPC .......... *G06F 3/0482* (2013.01); *G06F 3/0481* (2013.01); *G06F 9/451* (2018.02); *G06F 19/321* (2013.01); *G16H 30/20* (2018.01); *G16H 40/63* (2018.01); *G06F 3/0488* (2013.01); *G06F 3/04817* (2013.01)

(58) Field of Classification Search
CPC .... G06F 19/3418; G06F 19/321; G06F 9/451; G06F 17/211; G06F 19/324; G06F 9/452; G06F 3/0482; G06F 3/0481; G06F 3/0488; G06F 3/04817; H04L 67/025; G16H 40/63; G16H 30/20
See application file for complete search history.

(56) References Cited

U.S. PATENT DOCUMENTS

| | | |
|---|---|---|
| 5,452,416 A | 9/1995 | Hilton et al. |
| 8,189,888 B2 | 5/2012 | Takahashi |
| 8,789,205 B2* | 7/2014 | Ramaswamy ........ G06F 21/604 726/28 |
| 9,509,872 B2 | 11/2016 | Ozaki |
| 2009/0171692 A1* | 7/2009 | Zilberman ............. G16H 50/20 705/2 |
| 2010/0064077 A1 | 3/2010 | Chung |
| 2013/0057475 A1* | 3/2013 | Duggan .............. G06F 3/04886 345/168 |

(Continued)

FOREIGN PATENT DOCUMENTS

EP 2660684 A1 11/2013

OTHER PUBLICATIONS

Bio-Rad Laboratories, "ChromLab Software for NGC Chromatography Systems: Learn Data Evaluation Tools from the Experts", Feb. 1, 2016, YouTube, <URL: https://www.youtube.com/watch?v=RMUB5NY5kSI> retrieved Feb. 26, 2020. (Year: 2016).*

*Primary Examiner* — Christopher J Fibbi
(74) *Attorney, Agent, or Firm* — Daniel C. Housley

(57) ABSTRACT

A user input interface on a mobile device may employ a set of routines to control computing functions on a computer. Computing functions may be associated with elements of the user input interface, such that the elements may be used to control the associated computing functions. The associations of computing functions and user input interface elements may be stored in a database.

20 Claims, 8 Drawing Sheets

(56) References Cited

U.S. PATENT DOCUMENTS

| | | | |
|---|---|---|---|
| 2014/0035835 A1* | 2/2014 | Zhang | G06F 3/041 |
| | | | 345/173 |
| 2014/0059494 A1 | 2/2014 | Lee et al. | |
| 2015/0199109 A1 | 7/2015 | Lee | |
| 2017/0010771 A1 | 1/2017 | Bernstein et al. | |
| 2017/0220227 A1* | 8/2017 | Mark | H04L 67/42 |
| 2018/0036469 A1* | 2/2018 | Crnkovich | A61M 1/267 |
| 2018/0365025 A1* | 12/2018 | Almecija | G06F 3/04847 |

* cited by examiner

ADAPTABLE USER INPUT INTERFACE

BACKGROUND

The present disclosure relates generally to the field of computing function execution, and more particularly to generating a user input interface to control a software application.

Most modern application interfaces, especially modern healthcare application interfaces, include a wide variety of executable functions. Modern applications may offer a combination of standard keyboard shortcuts to execute the various computing functions and/or provide users the ability to configure keyboard shortcuts. A modern user interface may include some sort of graphical interface where icon-associated shortcuts may execute computing functions, and/or a dialog box that allows a user to select a function and then press a key or key-combination to associate the execution of the function, or a set of functions, with the key/key-combination.

SUMMARY

Disclosed herein are embodiments of a method, system, and computer program product for interacting with a computer via a user input interface on a mobile device.

A set of routines are executed on a computer to control a plurality of computing functions via a user input interface. A selected computing function of the computer is associated with at least one element of the user input interface, such that the at least one element controls the selected computing function. The association of the selected computing function is stored with the at least one element of the user input interface.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

Figure 1A:
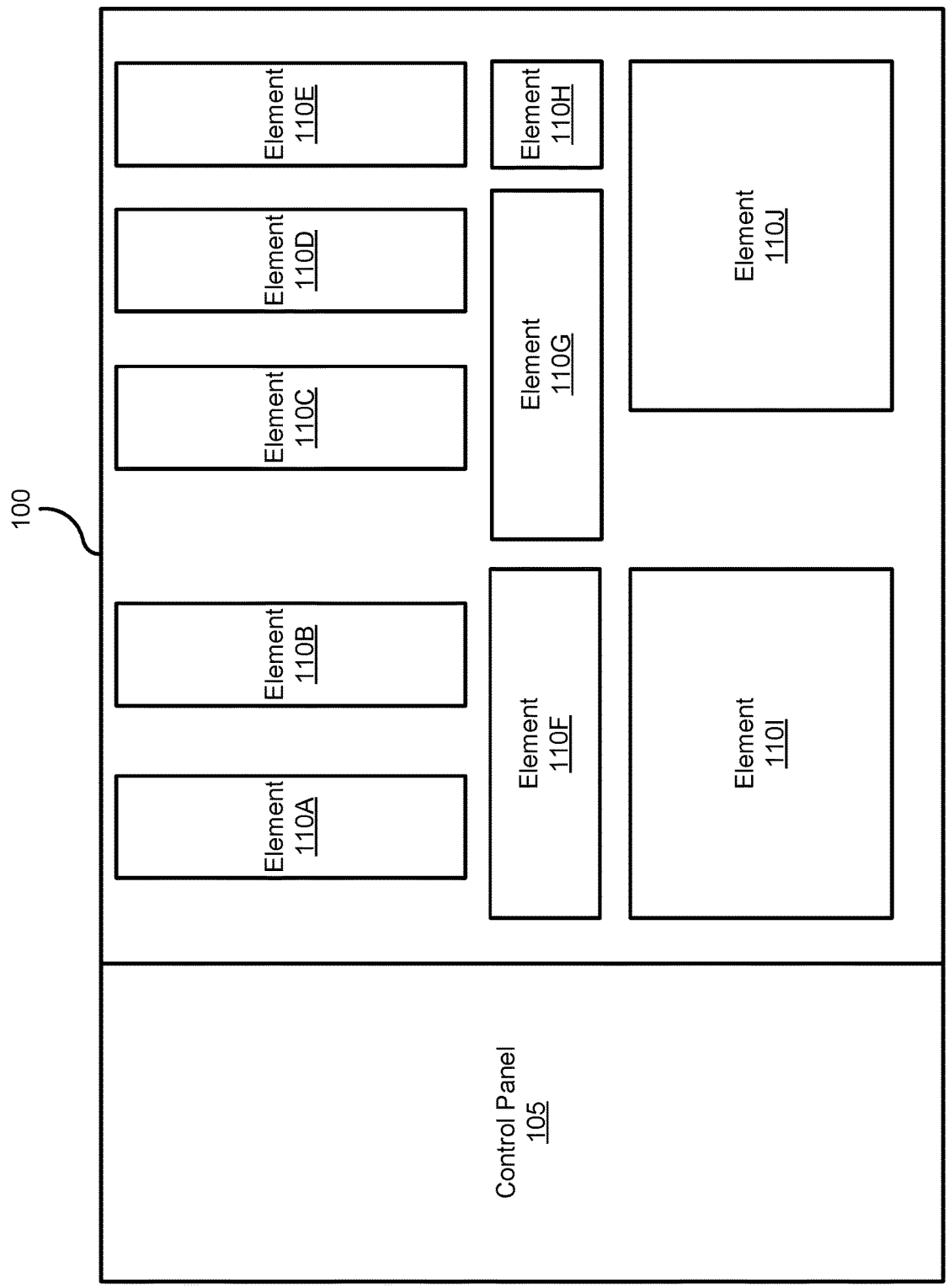
FIG. 1A depicts a block diagram of an example layout of a user input interface displayed on the touchscreen of an external controller device, according to embodiments.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the invention.

DETAILED DESCRIPTION

Aspects of the present disclosure relate to computing function execution, and more particularly to generating a user input interface to control a software application. While the present disclosure is not necessarily limited to such applications, various aspects of the disclosure may be appreciated through a discussion of various examples using this context.

Usability is one of the main concerns that application developers and designers keep in mind when creating new computer programs. The usability of an application is a key factor to determine the success of the application itself. This is particularly true for mobile applications. Users of mobile applications expect sophisticated design, high-fidelity and intuitive user interfaces, and high performance. These are the main reasons why native applications, those implemented directly on the operating system using the native Application Programming Interfaces (APIs) of the target mobile platform, have overtaken Web and hybrid applications, those written in HTML, CSS and JavaScript, and running on the device's browser. Mobile applications with poor usability tend to receive negative reviews and may eventually fail.

Usability is even more impactful in certain environments, such as, for example, healthcare applications. The main concern behind the usability of such applications is related less to success on the market, and related more to the fact that a poorly designed application, difficult to use and with an arcane user interface, may effectively hinder the functionality of the application itself. If a healthcare application is very difficult to use, a healthcare provider using it to examine a patient may make mistakes, or may inadvertently neglect to use advanced features of the application if such features are hard to access. This may eventually negatively affect the health of the patient and even lead to medical mistakes, worsening of the patient's health.

The present disclosure provides a method for generating shortcuts to an external controller device with interactive graphic display capability (e.g., user input interface), such as an IPAD or other computing tablet, or keyboard with LED/LCD keys or graphical touchscreens. In embodiments, a user may employ a stylus, fingers, or other tools for interacting with a touchscreen or other physical interface displaying one or more visual elements of a user input interface. The user may adjust the location, layout, and other attributes or specifications of the elements of the user input interface (UII) by activating a configuration mode via a dialog box, speech command, etc. The user may receive a visual or other confirmation that the configuration mode is active. In embodiments, the visual confirmation may be a change in appearance of the tools, a confirmation message, or the interactive tools or elements exhibiting animation (e.g., the elements may "shake"), or otherwise indicate that the configuration mode has been activated.

In embodiments, a graphical representation of a keyboard or of a target application's GUI may appear on the screen of the external controller device. In embodiments, a graphical representation of the UII may appear on a display coupled to a computer system running the target application. The user may drag an interface element to a depicted keyboard location to create a keyboard shortcut associated with that element. In embodiments, the user may drag a computing function from a representation of a target application's menu(s) and/or GUI to an interface element to create a shortcut associated with that interface element. A target application may be the application or a set of applications the user wants to control using the external controller device. The keyboard depiction or other representation may then be updated to include a reference to that element. The user may later recall the keyboard depiction or other representation to further configure the shortcuts, view them, copy them to another user's user input interface, etc. In embodiments, the computer system may be connected to a keyboard with LCD/LED keys, or keys that can otherwise be dynamically graphically modified, and the physical keyboard itself may be updated to represent the new element associations.

In embodiments, the external controller device may, via the UII, scan a target application to determine an array of computing functions by evaluating interactive elements of the target application's GUI and/or menus and populate a list of computing functions that a user may use to associate with interface elements.

In embodiments, an element may be an interactive area of a graphical user interface. For example, in embodiments, an element may be a clickable icon, a customizable and interactive polygon displayed on a touchscreen, etc. Similarly, the UII of the external controller device may automatically respond to a change in user, application, or other changes in conditions.

In embodiments, an IPAD or other computing tablet or smartphone device may be used as the external controller device and coupled to the computer system running the target application via a USB connection, WIFI connection, or any other physical or non-physical communicative connection with the computer system. In embodiments, an API may mediate the connection between the external controller device and the target application. In embodiments, the external controller device may employ macros to execute computing functions on the target application. In embodiments, when the configuration mode is active, the system may display a graphic or some other indicator to alert the user that the controller may be in a configuration mode. The user may drag one or more elements to an indicated location on the computer system screen to configure the layout/position/location of the elements of the UII. As a result, the elements on the UII of the external controller device may be configured so that the user can subsequently use the external controller device to execute computing functions in the target application. The computing system may store the configuration of the UII elements as rules or as a part of a computing function profile associated with the user.

In embodiments, the computing function profiles may be associated with one or more conditions. Conditions may include informative aspects that may impact the arrangement and type of elements displayed on the user input interface. For example, conditions may include the user's job title or role, the type of program being used, the type of tasks being performed by the target application, the subject of the particular task, the dimensions of a user's hand, ergonomic data related to the user, etc. Using an example of a medical imaging program as a target application, conditions may include the user's role (e.g., doctor, nurse, technologist, technician, etc.), the type of exam/image (e.g., image to diagnose knee pain, image to identify unknown mass, etc.), the imaging modality (e.g., MRI, X-ray, CT scan, etc.), body part (e.g., knee, brain, spine, lung, etc.), user characteristics (e.g., left-handed, poor vision, arthritis, carpal tunnel, etc.), etc. As a result, when subsequently used, the external controller device may, for example, display a layout of elements when a particular user is viewing a CT, then automatically switch to another layout when the user is viewing an MRI.

In embodiments, the configuration mode of the UII may employ machine learning to provide an automated configuration mode. In embodiments, the system may monitor the user's behavior to automatically determine a UII layout that may optimize the user's experience, according to conditions associated with the user. The system may further monitor user behavior to add, remove, or rearrange elements on the UII to refine and further optimize the user's experience.

The present disclosure enables users to arrange a graphic display (e.g., UII layout) of elements associated with the computing functions they desire and/or use most, and may be an aide to users with low vision, repetitive motion injuries, or other impairments, by compensating (e.g., enlarging elements/text, optimizing layout to minimize hand and finger motions, etc.) for an individual user's needs. The present disclosure may also decrease the learning curve associated with learning a new application, and thereby decrease training time for new users.

Turning now to the figures, FIG. 1A depicts a block diagram of an example layout of a user input interface displayed on the touchscreen of an external controller device 100, according to embodiments. In embodiments, the user input interface (UII) may be displayed on the touchscreen of a mobile computing device (e.g., an external controller device), such as a computing tablet device, smart phone, IPAD, or other mobile computing device. In embodiments, the device may include a touchscreen capable of displaying a number of icons/elements with attributes specified by a user or a user input interface generator, such as the UII generator 668 of FIG. 6. In embodiments, the size/shape/location/appearance and other attributes of elements may be predetermined by the UII generator, according to conditions associated with the user and/or according to monitored user behaviors.

In embodiments, the UII 100 may include a control panel 105. The control panel 105 may provide the user with the configuration tools necessary to generate UII elements, such as elements 110A-J, as well as the tools necessary to associate those elements with computing functions in the target application. Tools to generate UII elements may include tools to define the size/shape/color/location and other attributes of elements. Tools for associating elements with computing functions may include tools to identify the target application; cross-application drag-and-drop tools; and application program interface (API) routines, macros, or any other means for associating an input with a target application's computing function. Any number of elements may be generated, according to embodiments.

In embodiments, a virtual depiction of the UII may be generated and displayed, for configuration purposes, on a display connected to the computer system (e.g., the computer 602 of FIG. 6) hosting a target application. In embodiments, the computer system may detect the connection, via, for example, USB, BLUETOOTH, WIFI, or other communicative connection, of an external controller device (e.g., a mobile device with a UII) and, in response to such a connection, generate a virtual depiction of the UII that may be displayed on the computer system running the target application. In embodiments, a virtual depiction of the target application's interface may be displayed on the external controller device that is communicatively coupled to the computer system hosting the target application (e.g., a virtual depiction of the target application's interface may be displayed along with the UII on the external controller device). The virtual depictions may be used to facilitate the use of drag-and-drop tools to create associations between the target application's computing functions and the UII's elements. For example, a virtual depiction of the UII may be displayed on the computer hosting the target application, and a user may drag and drop the target application's computing function onto a virtual depiction of a UII element. For example, the user may drag and drop the "save" computing function from the target application onto element 110A, and thereafter, the user may execute the "save" function of the target application by interacting with element 110A. Each element 110A-J may be associated with a different computing function, or a set of computing functions, of one or more target applications.

In embodiments, the user input interface may include a peripheral device coupled to the computer system running the target application, such as an LED/LCD keyboard. In such embodiments, the size/shape of elements may not be customizable, but the appearance (e.g., backlighting, color, etc.) and location of the elements may be alterable according to user or generator specifications. For example, in such embodiments, the user may associate the target application's computing functions with the physical elements of the peripheral device. In such embodiments, the control panel 105 may be used to alter the appearance of the UII elements according to the user or UII generator's specifications. For example, if the embodiment employs an LED keyboard, the control panel 105 may be used to change the brightness, color, or other attributes of the particular element (e.g., key) according to the user's specifications or according to the UII generator's specifications. For example, the user or the UII generator may specify that the F12 key on an LED keyboard should be associated with the print function of the target application, and that the F12 key should glow orange at 50% brightness.

Figure 1B:
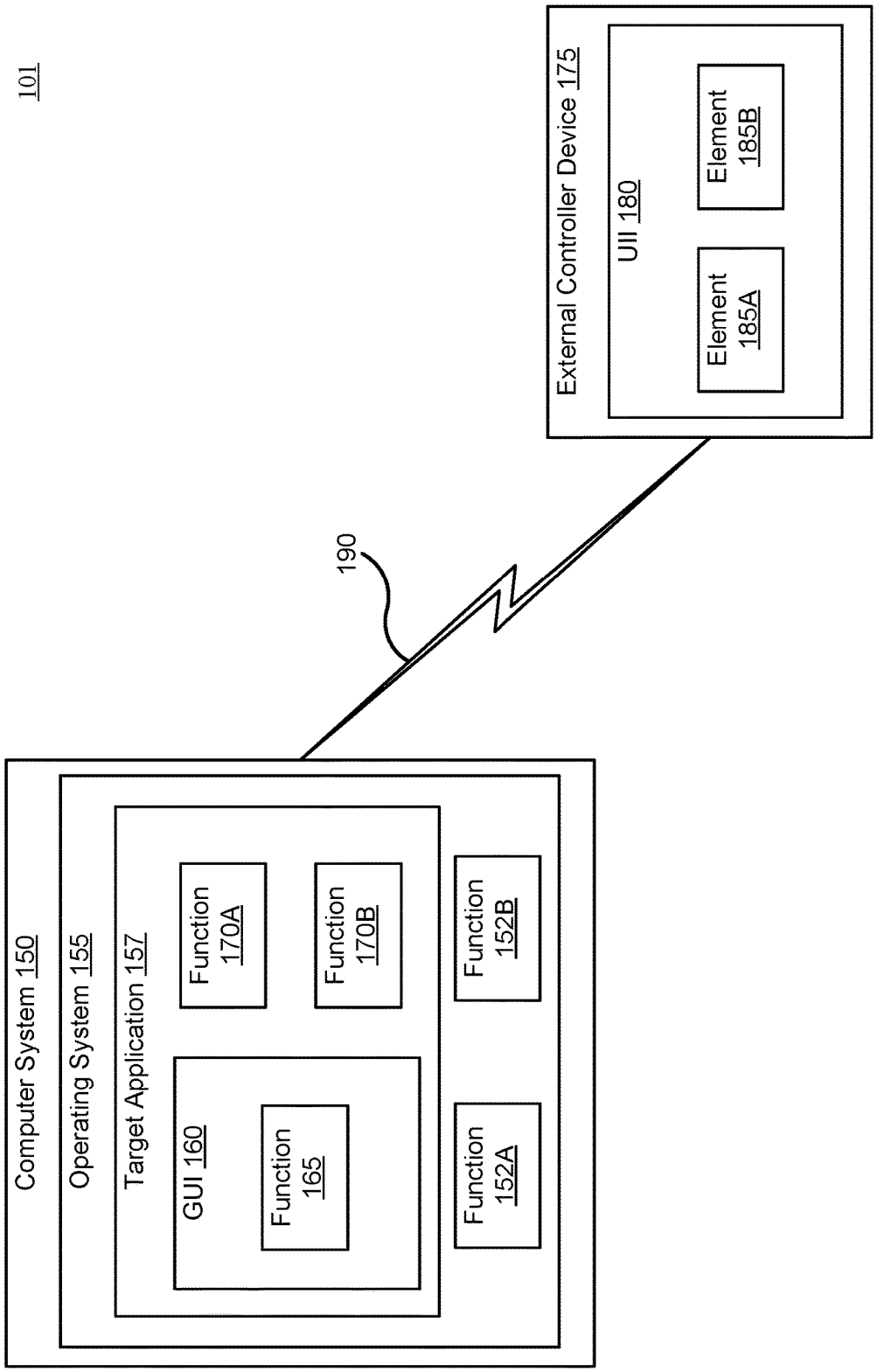
FIG. 1B depicts a block diagram of an example computing environment in which embodiments of the present disclosure may be implemented.

Turning now to FIG. 1B, depicted is a block diagram of an example computing environment 101 in which embodiments of the present disclosure may be implemented. In embodiments, a computer system 150 may be communicatively coupled to an external controller device 175 via connection 190. Computer system 150 may be, for example, a desktop computer, a medical imaging device, a laptop, or any other computing device capable of running an instance of an operating system and displaying a GUI, and may correspond to, for example, computer 602 of FIG. 6. External controller device 175 may be, for example, a computing tablet, smart phone, IPAD, or other computing device with a touchscreen, and may correspond to, for example, external controller device 620 of FIG. 6. Connection 190 may be, for example, a USB connection, WIFI connection, BLUETOOTH connection, or any other physical or non-physical communicative connection with the computer system 150. In embodiments, connection 190 may be achieved using any manner of network, such as, for example, the network 640 of FIG. 6.

Computer system 150 may include an operating system 155, and operating system 155 may be capable of running one or more target applications, such as target application 157. In addition, operating system 155 may be capable of executing computing functions native to the operating system, such as functions 152A-B. Computing functions native to the operating system 155 may include, for example, a system shutdown sequence, functions to start or terminate an application, or any other function typically associated with an operating system, such as, for example, WINDOWS, LINUX, MACOS, etc. Functions 152A-B may be associated with GUI elements (e.g., icons, menus, buttons, etc.), hotkey combinations, command line inputs, etc.

Target application 157 may run on operating system 155 and utilize the resources of computer system 150. In embodiments, a target application may be, for example, a medical image viewing program, a word processor, a web browser, or any other application capable of being controlled by an external controller device 175. Target application 157 may include a graphical user interface (GUI) 160 for receiving user input and displaying visual output. User input may be received via user interaction with the GUI 160 to execute computing function 165. In embodiments, computing function 165 may be, for example, an icon, a menu, a button, or any other interactive GUI element. In embodiments, user input may be received by the target application 157, but not via the GUI 160, to execute computing functions 170A-B. In embodiments, computing functions 170A-B may be associated with hotkey combinations, command line inputs, etc. Computing functions 165 and 170A-B may correspond to, for example, computing functions 612 A-B of FIG. 6.

Figure 6:
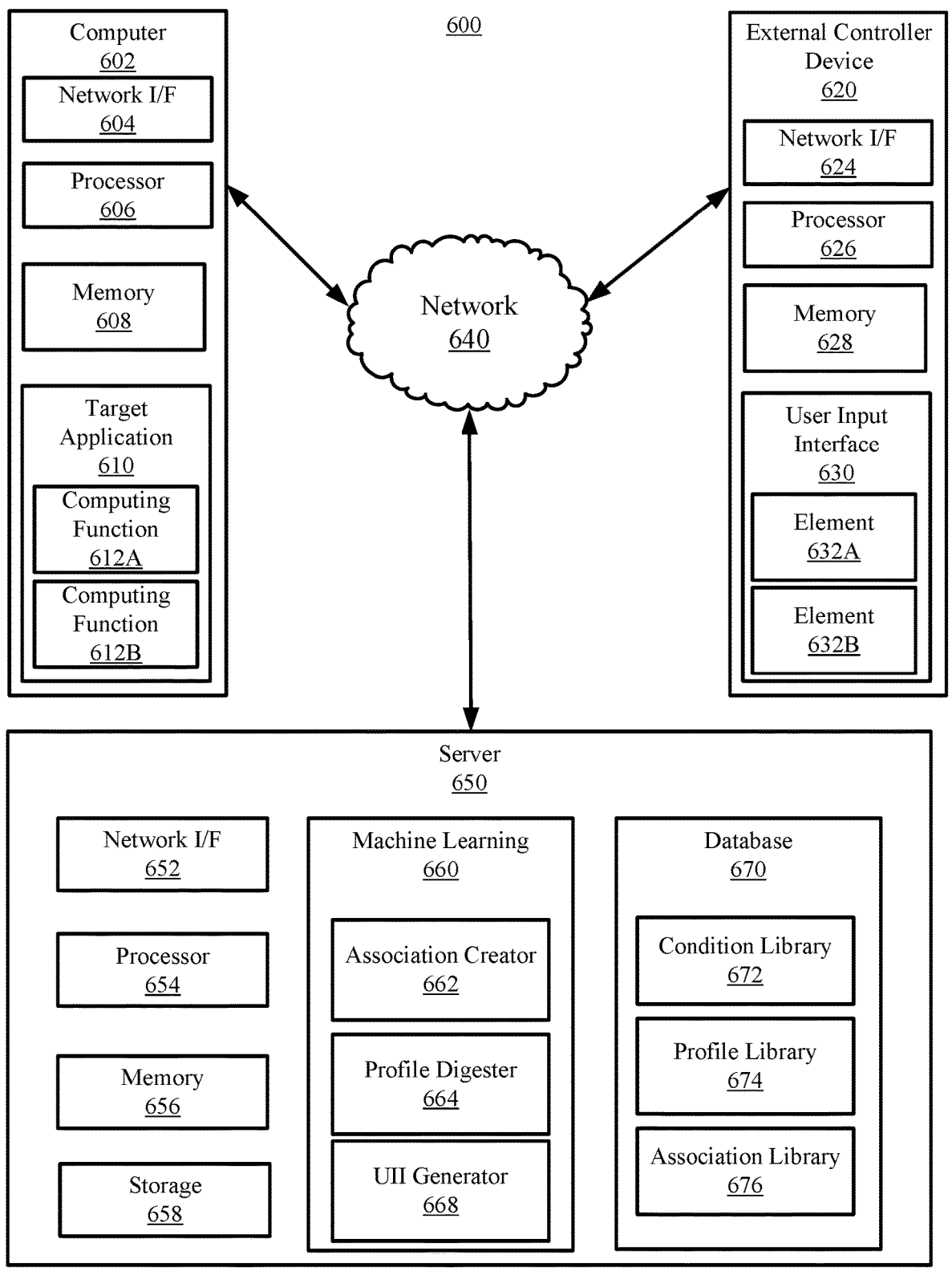
FIG. 6 depicts a block diagram of an example computing environment in which embodiments of the present disclosure may be implemented.

UII 180 may run on external controller device 175 and may correspond to UII 630 of FIG. 6. UII 180 may include interactive visual elements 185A-B, and visual elements 185A-B may correspond to elements 632A-B of FIG. 6. Visual elements 185A-B may be associated with computing functions 152A-B, 165, and 170A-B in such a way (e.g., using APIs, macros, etc.) that a user interaction with an element 185A-B may cause the execution of one or more of computing functions 152A-B, 165, and 170A-B, as described herein.

Figure 2:
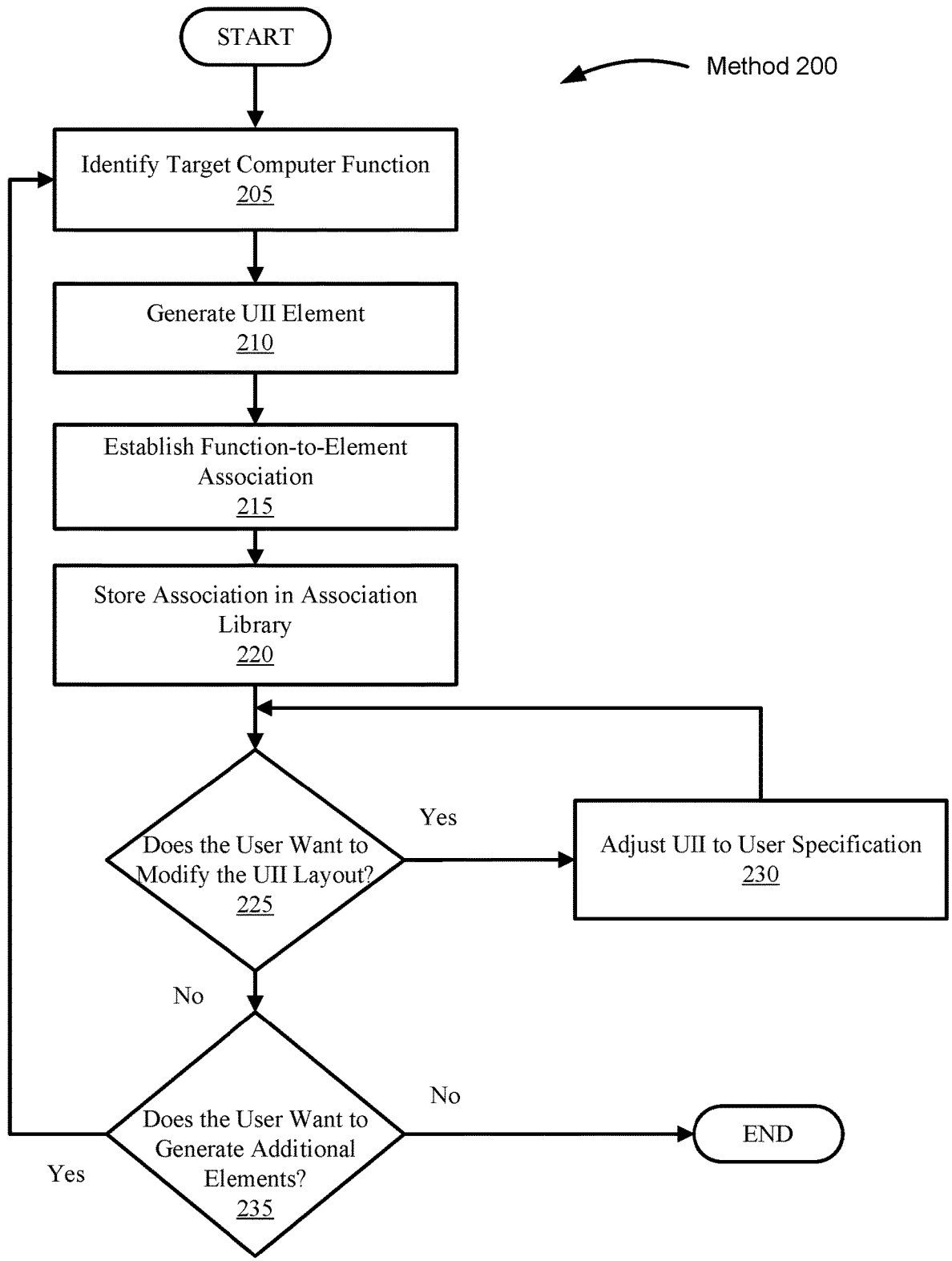
FIG. 2 illustrates a flowchart of a method for generating an element of a user input interface, the element associated with a computing function, according to embodiments.

Turning now to FIG. 2, illustrated is a flowchart of method 200 for generating an element of a user input interface, the element associated with a computing function, according to embodiments. At 205, a target computing function is identified. For example, a user may identify a particular program command/input (e.g., computing function). For example, a user may select a computing function, or set of computing functions, in an image viewing program that saves a particular image in a particular format to a particular location with a descriptive tag describing the image in the filename. For example, in a medical imaging environment, the command may save an X-ray image of a fractured humerus in .tiff format to a file folder containing a particular patient's medical chart, and the file name may be "[root_file_name]_fractured_humerus_xray.tiff."

At 210, a UII element is generated. Specifications for the UII element may be defined by the user or by the UII generator (e.g., the UII generator 668 of FIG. 6). For example, the user may specify and/or alter the size, shape, color, label, font size of the text label, font type, location, etc., or the element may be automatically generated by the UII generator. In embodiments, the UII generator may use information included in the user's computing function profile or, in the event that the user has no computing function profile or a limited computing function profile, the UII generator may use conditions related to the target application (e.g., the type of file opened in the target application, the type of computing functions being executed, etc.). Information included in the user's computing function profile may include information pertinent to creating an optimal UII configuration for a particular user. Pertinent information may include, for example, whether the user is right or left-handed, whether the user has a vision impairment, the user's job title, the user's job role, the user's preferences, computing functions frequently executed by the user, etc.

At 215, a function-to-element association is established. Establishing a function-to-element association may include creating a cross-application execution routine (e.g., API, macro, etc.) so that when a particular element of the UII is interacted with, the associated computing function of the target application is executed. In embodiments, sequences of computing functions may be created and associated with a single UII element. For example, in an environment where a serum protein electrophoresis (SPEP) graph is to be fractionated and quantified, interacting with a single UII element may cause the SPEP graph to be fractionated by curve minimums, and the areas under the graph's curves and between the minimums to be identified and quantified (e.g., using integral calculations). This may reduce the number of computing functions and/or shortcuts that must be executed, and/or the number of elements that must be interacted with to achieve the desired outcome.

At 220, the function-to-element association may be stored in an association library, such as the association library 676 of FIG. 6. In embodiments, stored associations may be further associated with one or more conditions, and thereby be used to automatically generate UII layouts and/or refine preexisting UII layouts.

At 225, it is determined whether the user wants to modify the UII layout. In embodiments, once a UII element is generated, the user may be asked whether he/she wishes to alter the element's attributes/specifications. Attributes and specifications may be blank by default, preset according to a standard, dictated by conditions, or they may be populated according to the user's most frequently used element attributes/specifications. An element's attributes and specifications may include, for example, the element's location on the UII, color, size, shape, text size, text font, etc. In embodiments, the user may further specify tactile or other feedback mechanisms. For example, in embodiments, the external controller device running the UII may provide localized vibrations or other sensations in response to a user interaction with a particular element. For example, the external controller device running the UII may include a plurality of vibration modules correlating to locations on the touchscreen of the device, and the vibration module or set of vibration modules most closely corresponding to the location of an element the user interacts with may vibrate in response to a user's interaction. In embodiments, the user may specify visual feedback mechanisms. For example, in embodiments, when an element is interacted with, the element may change color, size, shape, the shape of associated text, display an animation (e.g. the element may "shake," exhibit a radial pulse, bounce, bulge, etc.), etc. to alert the user and confirm the interaction.

If at 225, it is determined that the user wants to modify the UII layout, the UII is adjusted according the user's specifications at 230. In embodiments, modifications/adjustments may include an alteration in one or more elements' location, size, shape, label font size, color, etc.

At 235, it is determined whether the user wants to generate an additional UII element. The determination may be made via a dialogue box, receiving input from the user to manually create an additional element, receiving a voice command from the user to generate an additional element, etc.

Figure 3:
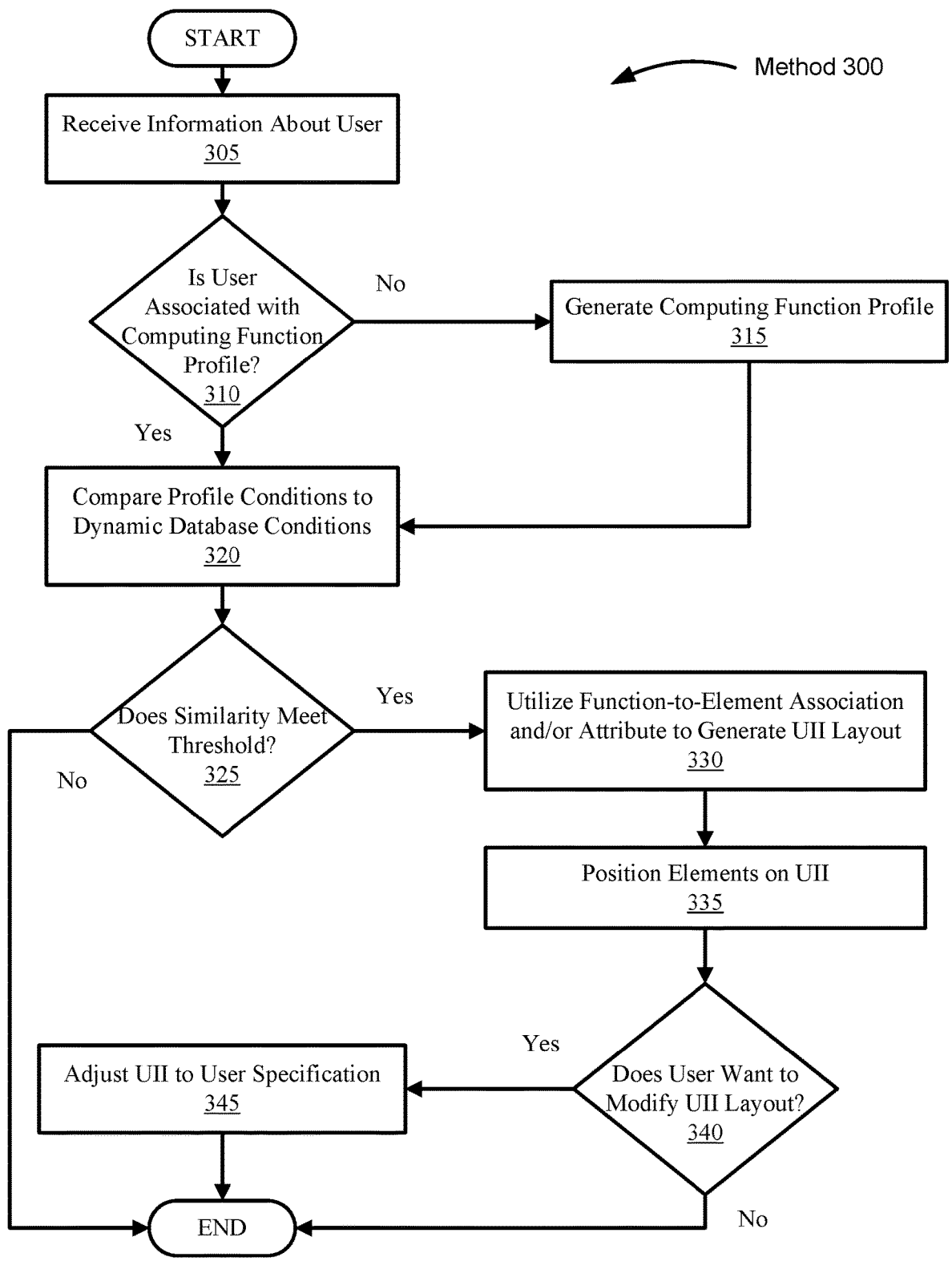
FIG. 3 illustrates a flowchart of a method for generating a user input interface layout based on a computing function profile, according to embodiments.

Referring now to FIG. 3, illustrated is a flowchart of a method for generating a user input interface layout based on conditions included in computing function profiles, according to embodiments. At 305, information about a user is received. The information may include, for example, a user identification and/or a set of conditions associated with a user. User identification may include a user's logon credentials, a voice print identification of the user (e.g., an audio sample obtained via a microphone attached to a computer, such as the computer 602 of FIG. 6), a visual identification of the user (e.g., a picture obtained via a camera attached to a computer, such as the computer 602 of FIG. 6), etc. Conditions may include, for example, user attributes relevant to generating a UII layout. Attributes may include, for example, whether the user is left or right-handed, the user's job title, job role, whether the user is visually impaired, specifics regarding a visual impairment (e.g., colorblindness, degree of myopia, blindness, macular degeneration, retinal detachment, nerve damage, etc.), whether the user has a physical impairment (e.g., missing limb, missing digits, motor function impairments, nerve damage, etc.), the type of computing functions the user uses most often, or any other attribute or condition mentioned herein or that may be relevant to generating a UII layout. In embodiments, the information may be a computing function profile containing a list of conditions already associated with a particular user.

At 310, it is determined whether the user is associated with a computing function profile. In embodiments, a computing function profile library, such as the profile library 674 of FIG. 6, may be queried to determine whether the user is associated with an existing computing function profile.

If, at 310, it is determined that the user is not associated with a computing function profile, a computing function profile may be generated at 315, according to information received at 305. For example, a computing function profile may be generated that stores associations between the user identification and conditions relevant to the user. For example, if a user's identification (e.g., logon username, employee identification, etc.) is 24601, and the information includes conditions of the user being left-handed, colorblind, and a medical technologist, then a computing function profile for user 24601 may be generated, and associations to the pertinent conditions (e.g., that the user is left-handed, colorblind, and a medical technologist) may be stored in the computing function profile. The user's computing function profile may be stored in a profile library, as discussed herein.

At 320, the conditions included in the computing function profile may be compared to conditions listed in a dynamic database of conditions. In embodiments, a dynamic database of conditions, such as the condition library 672 of FIG. 6, may include a dynamic list of the conditions associated with a plurality of users and/or a preset list of standard or common conditions. The conditions included in the dynamic database of conditions may be associated with function-to-element associations, such as the associations included in association library 676 of FIG. 6. In embodiments, comparisons may include simple condition-to-condition comparisons (e.g., each condition in the computing profile is compared to each condition included in the dynamic list of conditions), or multi-condition comparisons (e.g., sets of one or more comparisons are compared to one or more conditions in the dynamic list of conditions) to determine a similarity between the conditions in the user's computing function profile and the function-to-element associations and/or attributes of UII elements associated with conditions in the dynamic list of conditions. Similarities may be employed to determine which conditions and may be most relevant to creating an optimized UII layout for a particular user by analyzing the relationships between conditions and their related function-to-element associations.

At 325, it is determined whether the similarity meets a threshold. In embodiments, a similarity may be a percentage, a value, a distance metric result, standard deviation, confidence interval, statistical cluster valuation, etc. In embodiments, a threshold may be preset, defined by a user, or it may be determined using a statistical analysis, such as a bell curve, Poisson distribution, ANOVA/ANCOVA analysis, etc. For example, a threshold for the similarity of condition X may be set at 93% of total users; therefore, if 93% of all user profiles with condition X utilize a particular function-to-element association, or if the UII elements of 93% of users share an attribute (e.g., the elements have the same color, label font size, layout, etc.), then the similarity may be determined to meet the threshold.

If, at 325, the similarity meets the threshold, then the condition and its related function-to-element association may be used when generating a UII layout at 330. For example, if the similarity between condition Y and element attribute Z meets the threshold, then element attribute Z may be used when creating the UII elements for a user with condition Y. For example, if condition Y is myopia, element attribute Z is label font size of 20, then if the similarity meets the threshold, the UII elements generated for users with myopia may contain labels with a font size of 20. In embodiments, a single element may be associated with a plurality of attributes.

At 335, the elements are positioned on the UII. For example, UII elements may be positioned in a particular layout, such as, but not limited to, the layouts depicted in FIG. 1A and FIG. 1B. In embodiments, layouts may take into account ergonomic impacts of various UII layouts. For example, multiple UII layouts may be contemplated, and the UII layout with the smallest chance to produce a repetitive motion injury may be selected.

At 340, it is determined whether the user wants to modify the UII layout, as described herein.

If at 340, it is determined that the user wants to modify the UII layout, the UII is adjusted according the user's specifications at 345, as described herein. In embodiments, adjustments to the UII may include a determination whether the user wants to generate additional elements, as described herein.

Figure 4:
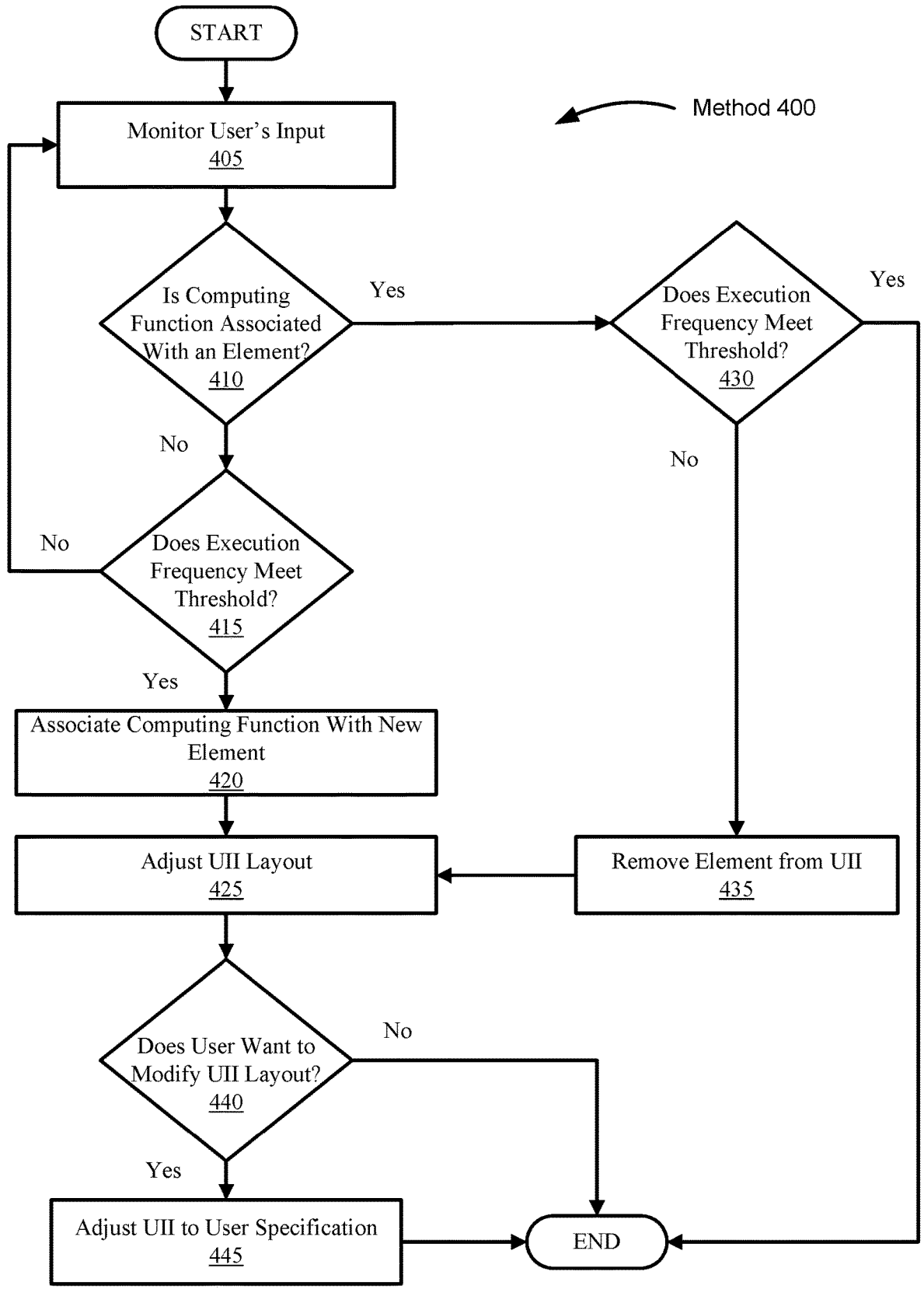
FIG. 4 illustrates a flowchart of a method for adding and removing elements from a user input interface based on monitored user input, according to embodiments.

Referring now to FIG. 4, illustrated is a flowchart of a method for adding and removing elements from a UII based on monitored user input, according to embodiments. At 405, a user's input is monitored. A user's input may include information regarding the computing functions a user executes.

At 410, it is determined whether the executed computing function is associated with a UII element. For example, it may be determined whether the computing function was executed via a UII element, or directly on the target application's interface.

If, at 410, it is determined that the computing function is not associated with an element, then it is determined, at 415, whether the frequency with which the user executes that computing function meets a frequency threshold. A frequency threshold may be, for example, the number of times a computing function is executed over a particular period of time. In embodiments, a frequency threshold may be the number of times the user executes a specific computing function during a single session of use of a target application. For example, a frequency threshold may include the number of times a user executes a specific computing function over a 30-min period, or a frequency threshold may include the number of times a user executes a specific computing function between the time the target application is opened and the time the target application is closed/terminated. In embodiments, a frequency threshold may include a real-time, dynamic calculation of the number of times a specific computing function is executed as a function of the overall time a user has been actively using the target application.

If, at 415, it is determined that the frequency threshold has been met, then the computing function is associated with a new UII element at 420. Associating the computing function with a new UII element may include storing the association in an association library, as described herein.

At 425, the UII layout is adjusted. For example, when a new UII element is created, a location, size, shape, and label for the element may be created and/or selected. The attributes/specifications may be designated by a user, or the attributes/specifications may be chosen by a machine learning module, such as the machine learning module 660 of FIG. 6, according to similarity thresholds, as described herein. When, for example, a UII element is eliminated, the attributes/specifications, such as the location, of the remaining UII elements may be updated to create an optimized layout.

If, at 410, it is determined that the computing function is associated with a UII element, then it is determined, at 430, whether the execution frequency of the computing function meets a frequency threshold, as described herein.

If, at 430, it is determined that the frequency threshold is not met, then the UII element is removed from the UII at 435. For example, if the UII includes an element associated with a computing function that a user executes less frequently over time, the element may be removed from the UII.

At 440, it is determined whether the user wants to modify the UII layout, as described herein.

If at 440, it is determined that the user wants to modify the UII layout, the UII is adjusted according the user's specifications at 445, as described herein. In embodiments, adjustments to the UII may include a determination whether the user wants to generate additional elements, as described herein.

Figure 5:
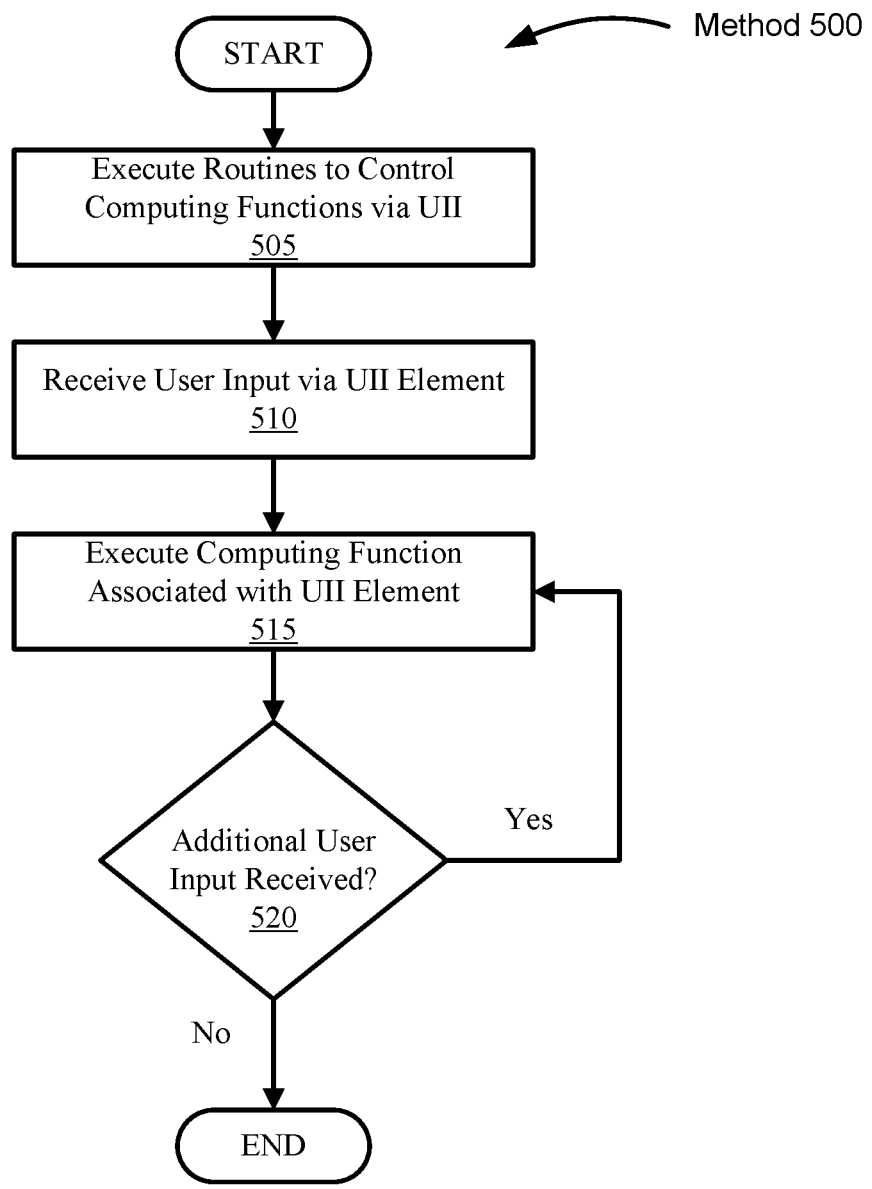
FIG. 5 illustrates a flowchart of a method for executing a computing function via a user input interface element, according to embodiments.

Referring now to FIG. 5, illustrated is a flowchart of a method 500 for executing a computing function via a user input interface element, according to embodiments. At 505, routines to control computing functions via a UII are executed. For example, API routines may be executed to allow a UII on an external controller device to control the computing functions of a target application on a computer system. For example, the API routines may allow a user to touch or otherwise interact with an icon, or other interactive polygon, on a portable computing tablet with a touchscreen, and consequently cause, in response to the interaction, a computing function of a target application running on a computer system coupled to the portable computing tablet, to be executed.

At 510, user input is received via a UII element. For example, the user may touch, or otherwise interact with, an icon (e.g., a UII element) displayed on the touchscreen of a portable computing tablet (e.g., an external controller device).

At 515, the computing function associated with the UII element is executed. A computing function may be, for example, any executable command of the target application. Examples of computing functions may include opening a file, saving a file, printing, rotating the content displayed on a monitor, flipping such displayed content, zooming in or out, closing the target application, or any other computing function traditionally executed via hotkey combination, clicking through GUI menus, entering command lines into a prompt, etc.

At 520, it is determined whether additional user input is received. For example, it is determined whether the user interacted with the same UII element again, or another UII element.

As discussed above, some embodiments may use machine learning. Accordingly, an understanding of the embodiments of the present disclosure may be aided by describing embodiments of machine learning systems and the environments in which these systems may operate. FIG. 6 illustrates a block diagram of an example computing environment 600 in which embodiments of the present disclosure may be implemented.

Consistent with various embodiments, the server 650, the computer 602, and the external controller device 620 may be computer systems. The server 650, the computer 602, and the external controller device 620 may include one or more processors 654, 606, and 626 and one or more memories 656, 608, and 628, respectively. The server 650, the computer 602, and the external controller device 620 may be configured to communicate with each other through an internal or external network interface 604, 624, and 652. The network interfaces 604, 624, and 652 may be, e.g., modems or network interface cards. The server 650, the computer 602, and the external controller device 620 may be equipped with a display or monitor (not pictured). Additionally, the server 650, the computer 602, and the external controller device 620 may include optional input devices (e.g., a keyboard, mouse, scanner, or other input device), and/or any commercially available or custom software (e.g., browser software, communications software, server software, natural language processing software, search engine and/or web crawling software, filter modules for filtering content based upon predefined parameters, etc.). In some embodiments, the server 650, the computer 602, and the external controller device 620 may be servers, desktops, laptops, or hand-held devices.

The server 650, the computer 602, and the external controller device 620 may be distant from each other and communicate over a network 640. In some embodiments, the server 650 may be a central hub from which the computer 602 and the external controller device 620 can establish a communication connection, such as in a client-server networking model. Alternatively, the server 650, the computer 602, and the external controller device 620 may be configured in any other suitable networking relationship (e.g., in a peer-to-peer configuration or using any other network topology).

In some embodiments, the network 640 can be implemented using any number of any suitable communications media. For example, the network 640 may be a wide area network (WAN), a local area network (LAN), an internet, or an intranet. In certain embodiments, the server 650, the computer 602, and the external controller device 620 may be local to each other, and communicate via any appropriate local communication medium. For example, the server 650, the computer 602, and the external controller device 620 may communicate using a local area network (LAN), one or more hardwire connections, a wireless link or router, or an intranet. In some embodiments, the server 650, the computer 602, and the external controller device 620 may be communicatively coupled using a combination of one or more networks and/or one or more local connections. For example, the computer 602 may be hardwired to the server 650 (e.g., connected with an Ethernet cable) while the external controller device 620 may communicate with the computer 602 and/or server 650 using the network 640 (e.g., over the Internet).

In some embodiments, the network 640 can be implemented within a cloud computing environment, or using one or more cloud computing services. Consistent with various embodiments, a cloud computing environment may include a network-based, distributed data processing system that provides one or more cloud computing services. Further, a cloud computing environment may include many computers (e.g., hundreds or thousands of computers or more) disposed within one or more data centers and configured to share resources over the network 640.

In some embodiments, the computer 602 and the external controller device 620 may enable users to submit (or may submit automatically with or without user input) information (e.g., computing function profiles, function-to-element associations, user behavior data, user preferences, etc.) to the server 650 to perform UII element generation, UII layout generation, computing function profile generation, user input monitoring, or any of the methods described herein.

In some embodiments, the server 650 may include a machine learning module 660. The machine learning module 660 may include an association creator 662, a profile digester 664, and a UII generator 668. The machine learning module 660 may include numerous subcomponents, such as a natural language processing system, a statistical comparator or distance metric analysis system, etc. Examples of methods that may be employed by the machine learning module 660 and its subcomponents are discussed in more detail in reference to FIGS. 2-5.

The association creator 662 may be configured to create associations between elements 632A-B of the UII 630 and computing functions 612A-B of the target application 610. In embodiments, any number of target applications 610, computing functions 612A-B, UIIs 630, and Elements 632A-B may be present or generated, as appropriate. When a function-to-element association is created, a user interaction with an element 632A-B will consequently cause the execution of the associated computing function 612A-B. For example, if element 632A is associated with computing function 612B, a user interaction with element 632A will execute computing function 612B. For example, if target application 610 is a word processor, element 632A is an element displayed on UII 630 and is associated with computing function 612A, and computing function 612A causes a footnote including a timestamp to be created, then a user interaction with element 632A will cause the word processor to create a timestamp footnote. Elements 632A-B may be associated with a single computing function 612A-B, or the elements 632A-B may be associated with any number of computing functions 612A-B, and the computing functions 612A-B may be combined in any order. Computing functions associated with UII elements may be executed on the target application 610 of computer 602 via APIs, macros, or any other means of associating the input of the external controller device's UII to the input of a target application.

The UII generator 668 may be configured to analyze information from user inputs, computing function profiles, function-to-element associations, etc. The UII generator 668 may include one or more modules or units, and/or may utilize the profile digester 664, to perform certain functions (e.g., parse and index information in computing profiles, process unstructured data into structured data via natural language processing techniques, identify a user, identify conditions associated with a user, monitor user behavior, etc.), as discussed in more detail in reference to FIGS. 2-5.

In some embodiments, the server 650 may include a database 670. The database 670 may be located in storage 658, or may be located separately. Database 670 may be a dynamic database, configured to store conditions (e.g., user attributes, target application attributes, application substrate attributes, etc.) in a condition library 672. Conditions may be indexed/referenced to function-to-element associations, particular users, etc. Using the example of a medical imaging application as a target application 610, conditions may include whether the user is right or left-handed, whether the user is vision-impaired, the job title or role of the user, whether the medical imaging application is an MRI viewing application versus an X-ray application versus a histological slide viewing application, etc., In some embodiments, the database 670 may include a profile library 674. The profile library 674 may be configured to store computing function profiles containing information regarding any number of users. Computing function profiles may be indexed/referenced to, and/or include, conditions, function-to-element associations, etc. Computing function profiles may further include user-specific preferences. For example, a particular user may prefer a particular arrangement/layout of UII elements 632A-B, and that preference may be stored in the user's computing function profile. In such a case, even if the machine learning module 660 determines that the user may benefit from a new UII element or an alternative layout, the preference stored in the user's computing function profile may inform, or override, the machine learning module to prevent the new UII element and/or layout from being generated.

In some embodiments, the server 650 may include an association library 676. The association library 676 may be configured to store the function-to-element associations of users. The association library 676 may be further configured to track usage data for each association to determine how useful an association may be (e.g., how often the element is used to execute the associated computing function, how many user actions are conserved as a result of the association, etc.). The associations stored in association library 676 may be indexed/referenced to the computing profiles of profile library 674 and/or the conditions of condition library 672. Consequently, the machine learning module 660 may utilize the database 670 and its components to monitor user behavior and suggest function-to-element associations based on frequency of element use, user preference, and conditions.

While FIG. 6 illustrates a computing environment 600 with a single server 650, a single computer 602, and a single external controller device 620, suitable computing environments for implementing embodiments of this disclosure may include any number of computers, external controller devices, and servers. The various models, modules, systems, and components illustrated in FIG. 6 may exist, if at all, across a plurality of computers, external controller devices, and servers. For example, some embodiments may include two servers. The two servers may be communicatively coupled using any suitable communications connection (e.g., using a WAN, a LAN, a wired connection, an intranet, or the Internet). The first server may include a machine learning module configured to create associations, digest computing profiles and other information, and generate UII elements and layouts, and the second server may include a database containing conditions, computing profiles, and associations.

It is noted that FIG. 6 is intended to depict the representative major components of an exemplary computing environment 600. In some embodiments, however, individual components may have greater or lesser complexity than as represented in FIG. 6, components other than or in addition to those shown in FIG. 6 may be present, and the number, type, and configuration of such components may vary.

Figure 7:
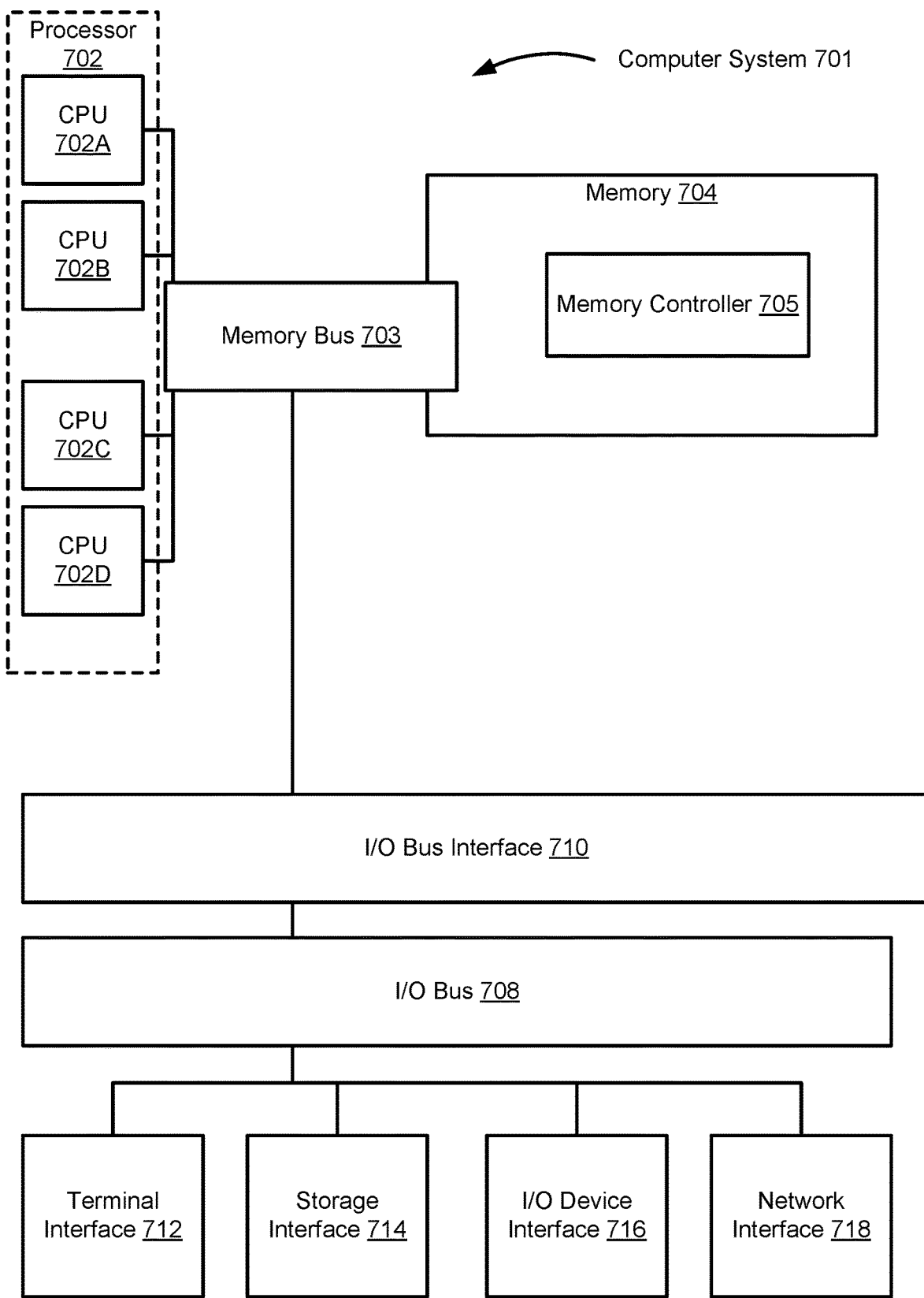
FIG. 7 illustrates a high-level block diagram of an example computer system that may be used in implementing embodiments of the present disclosure.

Referring now to FIG. 7, shown is a high-level block diagram of an example computer system (i.e., computer) 701 that may be configured to perform various aspects of the present disclosure, including, for example, methods 200/300/400/500, described in FIGS. 2-5, respectively. The example computer system 701 may be used in implementing one or more of the methods or modules, and any related functions or operations, described herein (e.g., using one or more processor circuits or computer processors of the computer), in accordance with embodiments of the present disclosure. In some embodiments, the major components of the computer system 701 may comprise one or more CPUs 702, a memory subsystem 704, a terminal interface 712, a storage interface 714, an I/O (Input/Output) device interface 716, and a network interface 718, all of which may be communicatively coupled, directly or indirectly, for inter-component communication via a memory bus 703, an I/O bus 708, and an I/O bus interface unit 710.

The computer system 701 may contain one or more general-purpose programmable central processing units (CPUs) 702A, 702B, 702C, and 702D, herein generically referred to as the CPU 702. In some embodiments, the computer system 701 may contain multiple processors typical of a relatively large system; however, in other embodiments the computer system 701 may alternatively be a single CPU system. Each CPU 702 may execute instructions stored in the memory subsystem 704 and may comprise one or more levels of on-board cache.

In some embodiments, the memory subsystem 704 may comprise a random-access semiconductor memory, storage device, or storage medium (either volatile or non-volatile) for storing data and programs. In some embodiments, the memory subsystem 704 may represent the entire virtual memory of the computer system 701, and may also include the virtual memory of other computer systems coupled to the computer system 701 or connected via a network. The memory subsystem 704 may be conceptually a single monolithic entity, but, in some embodiments, the memory subsystem 704 may be a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory may be further distributed and associated with different CPUs or sets of CPUs, as is known in any of various so-called non-uniform memory access (NUMA) computer architectures. In some embodiments, the main memory or memory subsystem 704 may contain elements for control and flow of memory used by the CPU 702. This may include a memory controller 705.

Although the memory bus 703 is shown in FIG. 7 as a single bus structure providing a direct communication path among the CPUs 702, the memory subsystem 704, and the I/O bus interface 710, the memory bus 703 may, in some embodiments, comprise multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 710 and the I/O bus 708 are shown as single respective units, the computer system 701 may, in some embodiments, contain multiple I/O bus interface units 710, multiple I/O buses 708, or both. Further, while multiple I/O interface units are shown, which separate the I/O bus 708 from various communications paths running to the various I/O devices, in other embodiments some or all of the I/O devices may be connected directly to one or more system I/O buses.

In some embodiments, the computer system 701 may be a multi-user mainframe computer system, a single-user system, or a server computer or similar device that has little or no direct user interface, but receives requests from other computer systems (clients). Further, in some embodiments, the computer system 701 may be implemented as a desktop computer, portable computer, laptop or notebook computer, tablet computer, pocket computer, telephone, smart phone, mobile device, or any other appropriate type of electronic device.

It is noted that FIG. 7 is intended to depict the representative major components of an exemplary computer system 701. In some embodiments, however, individual components may have greater or lesser complexity than as represented in FIG. 7, components other than or in addition to those shown in FIG. 7 may be present, and the number, type, and configuration of such components may vary.

The programs described herein are identified based upon the application for which they are implemented in a specific embodiment of the disclosure. However, it should be appreciated that any particular program nomenclature herein is used merely for convenience, and thus the disclosure should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for interacting with a computer via a user input interface on a mobile device, the method comprising:
   executing, on the computer, a set of routines to control a plurality of computing functions via the user input interface;
   evaluating a plurality of interactive elements of a target application on the computer to determine a subset of the plurality of computing functions;
   associating a selected computing function, from the subset of the plurality of computing functions, of the computer with at least one element of the user input interface, such that the at least one element controls the selected computing function;
   storing the association of the selected computing function with the at least one element of the user input interface, wherein storing the association further comprises relating the association to a condition in a dynamic database of conditions, wherein each condition is related to one or more associations, and wherein each condition comprises a specific user, a user role, a user attribute, a computer program, a set of computing functions, a dominant hand for the specific user, and a set of ergonomic data for the specific user;
   activating, in response to an input from a first user, a configuration mode;
   scanning one or more menus of the target application to identify a second subset of the plurality of computing functions;
   generating a graphical representation of the second subset of the plurality of computing functions; and
   receiving, from the first user during the configuration mode, a set of configuration adjustments for the user input interface, wherein the set of configuration adjustments includes user-specified attributes for the size, shape, color, label, and font type and size of the label text of each of the at least one element of the user input interface and a user selection of one or more of the computing functions of the second subset to generate an association with a second element of the user input interface.

2. The method of claim 1, further comprising:
   displaying the at least one element associated with the computing function at a location on the user input interface to account for the dominant hand for the specific user and the set of ergonomic data for the specific user by minimizing the hand and finger motions of the specific user;
   receiving input interacting with the location on the user input interface; and
   executing the selected computing function associated with the at least one element of the user input interface.

3. The method of claim 2, wherein the storing the association comprises storing an indication to display the at least one element at the location on the user input interface and wherein the displaying the element at the location occurs in response to the stored indication.

4. The method of claim 2, further comprising:
   monitoring user input;
   determining, based upon the monitored input, that the frequency of the user's execution of a second computing function meets a threshold;
   associating the second computing function with a second element; and
   displaying the second element on the user input interface.

5. The method of claim 2, further comprising:
   monitoring user input;
   determining, based upon the monitored input, that the frequency of the user's execution of a computing function does not meet a threshold;
   terminating the association of the computing function to the element; and
   removing the element from the display of the user input interface.

6. The method of claim 2, wherein the element is an icon displayed on a touchscreen.

7. The method of claim 6, wherein the condition comprises an exam type, an imaging modality, a body part, and a pathology.

8. The method of claim 1, wherein the method further comprises:
   receiving information about the first user;
   analyzing the information to generate a computing function profile tailored to the first user, the computing function profile including a set of conditions;
   determining, based on the dynamic database of conditions, the associations related to the set of conditions;
   associating, based on the one or more associations related to the set of conditions, a set of computing functions with a set of user input interface elements; and
   displaying the set of user input interface elements on the user input interface.

9. The method of claim 8, further comprising:
   monitoring the dynamic database of conditions;
   altering, based on changes in the dynamic database of conditions, the set of user input interface elements displayed on the user input interface.

10. The method of claim 1, wherein the user input interface is a touchscreen.

11. The method of claim 1, wherein the at least one interactive element is associated with a graph fractionation and quantification function.

12. The method of claim 1, wherein the computing functions include medical image viewing routines.

13. The method of claim 1, wherein the set of ergonomic data for the specific user includes a set of physical and visual impairments.

14. A system for interacting with a computer via a user input interface on a mobile device, the system comprising:
a memory with program instructions stored thereon; and
a processor in communication with the memory, wherein the system is configured to perform a method, the method comprising:
executing, on the computer, a set of routines to control a plurality of computing functions via the user input interface;
evaluating a plurality of interactive elements of a target application on the computer to determine a subset of the plurality of computing functions;
associating a selected computing function, from the subset of the plurality of computing functions, of the computer with at least one element of the user input interface, such that the at least one element controls the selected computing function;
storing the association of the selected computing function with the at least one element of the user input interface, wherein storing the association further comprises relating the association to a condition in a dynamic database of conditions, wherein each condition is related to one or more associations, and wherein each condition comprises a specific user, a user role, a user attribute, a computer program, a set of computing functions, a dominant hand for the specific user, and a set of ergonomic data for the specific user;
activating, in response to an input from a first user, a configuration mode;
scanning one or more menus of the target application to identify a second subset of the plurality of computing functions;
generating a graphical representation of the second subset of the plurality of computing functions; and
receiving, from the first user during the configuration mode, a set of configuration adjustments for the user input interface, wherein the set of configuration adjustments includes user-specified attributes for the size, shape, color, label, and font type and size of the label text of each of the at least one element of the user input interface and a user selection of one or more of the computing functions of the second subset to generate an association with a second element of the user input interface.

15. The system of claim 14, wherein the method further comprises:
displaying the at least one element associated with the computing function at a location on the user input interface to account for the dominant hand for the specific user and the set of ergonomic data for the specific user by minimizing the hand and finger motions of the specific user;
receiving input interacting with the location on the user input interface; and
executing the selected computing function associated with the at least one element of the user input interface.

16. The system of claim 15, wherein the storing the association comprises storing an indication to display the element at the location on the user input interface and wherein the displaying the element at the location occurs in response to the stored indication.

17. The system of claim 14, wherein the method further comprises:
receiving information about the first user;
analyzing the information to generate a computing function profile tailored to the first user, the computing function profile including a set of conditions;
determining, based on the dynamic database of conditions, the associations related to the set of conditions;
associating, based on the one or more associations related to the set of conditions, a set of computing functions with a set of user input interface elements; and
displaying the set of user input interface elements on the user input interface.

18. The system of claim 17, wherein the method further comprises:
monitoring the dynamic database of conditions;
altering, based on changes in the dynamic database of conditions, the set of user input interface elements displayed on the user input interface.

19. The system of claim 14, wherein the set of ergonomic data for the specific user includes a set of physical and visual impairments.

20. A computer program product for interacting with a computer via a user input interface on a mobile device, the computer program product comprising a computer readable storage medium having program instructions embodied therewith, the program instructions executable by a device to cause the device to:
executing, on the computer, a set of routines to control a plurality of computing functions via the user input interface;
evaluating a plurality of interactive elements of a target application on the computer to determine a subset of the plurality of computing functions;
associating a selected computing function, from the subset of the plurality of computing functions, of the computer with at least one element of the user input interface, such that the at least one element controls the selected computing function;
store the association of the selected computing function with the at least one element of the user input interface, wherein storing the association further comprises relating the association to a condition in a dynamic database of conditions, wherein each condition is related to one or more associations, and wherein each condition comprises a specific user, a user role, a user attribute, a computer program, a set of computing functions, a dominant hand for the specific user, and a set of ergonomic data for the specific user;
activate, in response to an input from a first user, a configuration mode;
scan one or more menus of the target application to identify a second subset of the plurality of computing functions;
generate a graphical representation of the second subset of the plurality of computing functions; and
receiving, from the first user during the configuration mode, a set of configuration adjustments for the user input interface, wherein the set of configuration adjustments includes user-specified attributes for the size, shape, color, label, and font type and size of the label text of each of the at least one element of the user input interface and a user selection of one or more of the computing functions of the second subset to generate an association with a second element of the user input interface.

* * * * *